United States Patent [19]
Ward et al.
[11] Patent Number: 4,571,290
[45] Date of Patent: Feb. 18, 1986

[54] PROCESS FOR THE SELECTIVE OXIDATION OF OLEFINS WITH PHOTOCHEMICAL ILLUMINATION OF SEMICONDUCTOR POWDER SUSPENSIONS

[75] Inventors: Michael D. Ward, South Euclid; James F. Brazdil, Jr., Mayfield Village; Robert K. Grasselli, Aurora, all of Ohio

[73] Assignee: The Standard Oil Company (Ohio), Cleveland, Ohio

[21] Appl. No.: 643,149

[22] Filed: Aug. 22, 1984

[51] Int. Cl.[4] .............................................. B01J 19/12
[52] U.S. Cl. ........................... 204/157.69; 204/157.9; 204/157.93
[58] Field of Search ....................... 204/158 R, 162 R

[56] References Cited

U.S. PATENT DOCUMENTS

| | | | |
|---|---|---|---|
| 3,301,905 | 1/1967 | Riemenschneider et al. | 204/162 R |
| 4,264,421 | 4/1981 | Bard et al. | 204/157.1 R |
| 4,303,486 | 12/1981 | Bard et al. | 204/162 R |
| 4,383,904 | 5/1983 | Shepherd | 204/158 R |

FOREIGN PATENT DOCUMENTS

| | | | |
|---|---|---|---|
| 0152834 | 9/1983 | Japan | 204/158 R |
| 7013639 | 9/1970 | Netherlands | 204/158 R |

*Primary Examiner*—Howard S. Williams
*Attorney, Agent, or Firm*—J. G. Curatolo; L. W. Evans

[57] ABSTRACT

A process for the selective oxidation of olefins comprises the steps of forming a suspension of semiconductor powder in a solvent media, adding an olefin to the solvent media in the presence of an oxidant to form a mixture and, photochemically activating the mixture with illumination having an energy at least equal to the band gap of the semiconductor powder wherein the selectivity is controlled by the selection of A, of the solvent and of the oxidant. The process is one carried out at about ambient temperature and with gentle agitation. The semiconductor powder has the general formula $A_xB_yC_z$ where A is selected from Bi, Sn, Pt, Pd, Cu, Fe, W, V, Sb, Mo, Ru or Ag and mixtures thereof; B is Te, Sb, Ti, Cd, Mo, V or W and mixtures thereof; C is O or S; x equals 0 to 5; y equals 1 to 3; and z is a number necessary to satisfy the other elements, and is optionally metallized by an element selected from Pt, Pd, Cu or Ag.

32 Claims, No Drawings

PROCESS FOR THE SELECTIVE OXIDATION OF OLEFINS WITH PHOTOCHEMICAL ILLUMINATION OF SEMICONDUCTOR POWDER SUSPENSIONS

TECHNICAL FIELD

The subject invention relates to a new and useful process for the selective oxidation of olefins with a photocatalytically activated semiconductor powder suspension at about ambient temperature and in the presence of an oxidant. This photoactivation is achieved with illumination having an energy at least equal to the band gap of the selected semiconductor powder.

BACKGROUND ART

The use of photocatalysis to prepare metallized semiconductor powders, such as $TiO_2$ powder metallized with copper, is described in U.S. Pat. No. 4,264,421. These catalysts have utility, for example, in the photocatalytic decarboxylation of saturated carboxylic acid. Metallizing of the semiconductor powder is disclosed as being achieved with illumination from a 2500 Watt Hg—Xe lamp operated at 1600 Watts for less than about four hours.

Such a method for the decarboxylation of saturated carboxylic acids on n-type semiconductor powders (e.g., $TiO_2$) is described in a companion patent, U.S. Pat. No. 4,303,486. The major reaction products are the corresponding alkanes and $CO_2$. A suspension of the catalyst in a solution containing the acid is irradiated at ambient temperature. The reaction mixture can be subjected to irradiation in the presence or absence of oxygen and the semiconductor powder, such as $TiO_2$, can be platinized.

Lastly, in Netherlands Pat. No. 7,013,639 there is disclosed the oxidation of hydrocarbons, such as isobutane, in gaseous or vapor phase, said hydrocarbon being passed, admixed with oxygen and at a temperature of not more than 100° C., over a metal oxide catalyst such as $TiO_2$ irradiated with UV light, to produce acetone.

Despite the teachings of the art, there has not been a recognition of the use of specific semiconductor powders for the selective oxidation of olefins, by photochemically activating a suspension of the semiconductor powder, the olefin and a suitable solvent.

SUMMARY OF THE INVENTION

The process for the selective oxidation of olefins comprises the steps of first forming a suspension of a semiconductor powder in a solvent media. The semiconductor powder has the general formula $A_xB_yC_z$ where A is selected from Bi, Sn, Pt, Pd, Cu, Fe, W, V, Sb, Mo, Ru or Ag and mixtures thereof; B is Te, Sb, Ti, Cd, Mo, V or W and mixtures thereof; C is O or S; x equals 0 to 5; y equals 1 to 3; and z is a number necessary to satisfy the other elements, and is optionally metallized by an element selected from Pt, Pd, Cu or Ag. The process steps include adding an olefin to the suspension in the presence of an oxidant to form a mixture and, photochemically activating the mixture with illumination having an energy at least equal to the band gap of the semiconductor powder wherein the selectivity is controlled by the selection of A, of the solvent and of the oxidant.

PREFERRED EMBODIMENT FOR CARRYING OUT THE INVENTION

The process of the present invention is useful for the oxidation of olefins to epoxides, alcohols, aldehydes and ketones. Suitable olefins are those having from two to about 20 carbon atoms including substituted species and cyclic compounds. Typical olefins include ethylene, propylene, 1-butene, 1-pentene, 1-hexene, 1-heptene, 1-octene, 1-nonene, 1-decene, cis and trans 2-butene, isobutylene, cis and trans 2-pentene, 3 methyl-1-butene, 2 methyl-2-butene, 2, 3, dimethyl-2-butene, 1,4 pentadiene, 1,5 hexadiene, 1,3 butadiene, 1,3 pentadiene, 2-methyl-1,3 butadiene, 2,3, dimethyl-1,3-butadiene, 1,2 propadiene, cyclopentene, 1,3 cyclopentadiene, cyclohexene, 1,3 cyclohexadiene, 1,4 cyclohexadiene, 3-ethylcyclopentene, bicyclo [2.2.2]octa-2-ene, norbornene and the like. The foregoing description and disclosure of suitable olefins are meant to be illustrative only of the many examples of olefins which can be oxidized by the subject process but should not be construed as exhaustive or limiting.

Desirable unsaturated aldehydes such as acrolein and methacrolein can be prepared, for example, from propylene and isobutylene, respectively. As will be noted hereinbelow, the selectivity for a given oxidation product can be controlled by the composition of a particular catalyst, as well as the oxidant and the solvent media. Gaseous, liquid or solid state olefins can be employed so long as they can be oxidized in the liquid phase.

In general, the process of this invention is carried out in a slurry reactor using an illuminated suspension of a semiconductor powder as a photocatalyst in a solvent media that is aqueous, organic, or mixture thereof. The selection of solvent media is important, since, for example, although water is required for the selective conversion of olefins to epoxides, in the absence of water, the conversion of olefins to saturated or unsaturated aldehydes is favored. This process can also be run in a recycle mode in order to increase the conversion of the starting olefin or substituted olefin to the desired product(s).

The general formula of semiconductor materials which can be utilized in the practice of this invention is $$A_xB_yC_z$$

where

A is Bi, Sn, Pt, Pd, Cu, Fe, W, V, Sb, Mo, Ru or Ag and mixtures thereof;

B is Te, Sb, Ti, Cd, Mo, V or W and mixtures thereof;

C is O or S;

x is 0 to 5;

y is 1 to 3 and, z is a number necessary to satisfy the other elements.

The optional A component, where x is greater than 0, can be provided in one of two manners. First, it can be in the catalyst wherein the material comprises elements A and B as mixed oxides or sulfides, depending on what C is, and where it may behave as a redox couple. Second, it can be in the reaction suspension as a redox couple wherein it is available to oxidize reduced species as they arise. At least some of the A elements namely, Pt, Pd, Cu and Ag, can also be employed as a metallized coating on the surface of the semiconductor powder. Metallized e.g., plantinized, semiconductor powder can be obtained by methods known in the art such as set forth in U.S. Pat. No. 4,264,421, the subject matter of which is incorporated herein by reference.

The A component, when used, is generally present as a soluble species in the solvent media but may also be incorporated into the solid matrix of the photocatalyst. The only requirement is that efficient contact between the surface of the photocatalyst and the component be maintained. Incorporation into the solid matrix of the semiconductor powder can be achieved by combining solutions of the two and allowing the solvent to evaporate. When employed as a soluble species, the desired A component can be added as a salt e.g., cupric nitrate hydrate to the semiconductor/solvent/olefin suspension.

Generally, preparation of the semiconductor material is not a feature of the present invention inasmuch as those skilled in the art can readily select the disclosed semiconductor powders and utilize the redox couple in one of the foregoing three manners by following known techniques. Thus, the particular steps of incorporating into the solid matrix, forming a suspension or metallizing are not to be construed as limitations of the present invention.

Although the subject invention has been exemplified with $TiO_2$ as the semiconductor powder, other semiconductors formed by combinations of the A, B and C components can be employed. Several of these, for instance, include $MoO_3$, $WO_3$, CdS and $CuMoO_4$. The semiconductor powder can also be modified, as for instance, by metallizing with platinum or by mixing with another powder such as $TiO_2$ and $MoO_3$ employed in Example No. 7 hereinbelow.

With respect to the solvent media, water can be employed alone or organic solvents for the olefins such as acetonitrile can be employed alone. Mixtures of water and organic solvents can also be employed and will further modify selectivity. Generally, the use of water will provide selectivity to the corresponding epoxide while organic solvents will provide aldehydes.

The light energy utilized to illuminate the semiconductor photocatalyst should have an energy greater than or equal to the band gap of the semiconductor photocatalyst. A typical light source that can be utilized is a 500 watt mercury lamp. The selected illuminating source and application thereof is not critical, it can vary as to type, intensity, positioning and time of application. Depending on how applied to a selected system, the illuminating source may contribute some acceptable amount of heat to the heat of reaction which is normally low.

The oxidation reaction of this invention may be accomplished by illumination of a stirred suspension of semiconductor powder with a 500 W mercury lamp; olefin is introduced by bubbling a stream of the olefin through the suspension if the olefin is volatile; or it is added directly to the suspension prior to or during illumination if the olefin is a liquid at ambient conditions.

The reaction requires the presence of an oxidant such as $O_2$, $H^+$ and/or reducible metal ions e.g., $Cu^{2+}$, $Fe^{3+}$ and the like, provided by the A component. When $O_2$ is employed, it is either present in the olefin stream (for volatile olefin) or in a sealed reaction vessel (for liquid olefin). The choice of oxidant also influences the product distribution. The presence of more than one oxidant in the reaction mixture also affects the product distribution. Where the process is conducted in an inert atmosphere such as $N_2$ and oxygen is not present, A component metals such as copper, present as a soluble species, will provide the oxidant.

A preferred example of the invention is directed toward the oxidation of propylene. The exemplary semiconductor powder was titanium oxide, $TiO_2$ (surface area $\leqq 50\ m^2/g$). When an aqueous suspension of $TiO_2$, that is $TiO_2$ in deionized water as solvent, was illuminated and a propylene-oxygen stream was bubbled through the mixture, acetaldehyde and propylene oxide were the major products, in a 4:1 ratio. When $cu^{2+}$ replaced $O_2$ as the oxidant (the reaction was performed with a propylene-$N_2$ stream) this selectivity changed to 1:4 and propionaldehyde, acrolein and larger amounts of allyl alcohol were observed. Other reducible species, such as ferrid ($Fe^{3+}$) ion or ferricyanide ion $Fe(CN)_6^{3-}$exhibited similar patterns in reaction selectivities.

This invention also includes the simultaneous presence of two oxidants. In reactions containing both $O_2$ and $Cu^{2+}$ ion, the selectivity shifted toward propylene oxide compared to $O_2$ alone, consistent with the above behavior. A modified catalyst, for example, plantinized $TiO_2$, was utilized with $H^+$ ion as an oxidant. In this case, acetaldehyde selectivity was only one percent and propylene oxide, propionaldehyde and allyl alcohol were also produced. Other modifications, such as incorporating $MoO_3$, $Sb_2O_4$ or $Sb_6O_{13}$ onto $TiO_2$, resulted in photocatalysts which exhibited enhanced selectivities for propylene oxide relative to acetaldehyde.

The following examples are representative employing $TiO_2$ as the semiconductor photocatalyst; products selectivities have been reported by mole percent unless otherwise specified and were determined by dividing the moles of aldehyde or other products formed by the moles of propylene fed $\times$ 100. Examples No. 1 to 7 were conducted in aqueous media.

EXAMPLE NO. 1

To a 100 ml water cooled reaction flask was added 100 mg $TiO_2$ semiconductor powder and 10 ml deionized water as solvent to produce a suspension that ws purged with $O_2$ for 10 minutes; propylene was then introduced to the $O_2$ gas stream and the propylene-oxygen ratio adjusted to 1:4, respectively; the flow rate through the suspension was 12 cc/min. The resulting reaction mixture was then illuminated with a 500 watt mercury lamp for 3 hours. Gas chromotographic analysis of the aqueous suspension after filtration showed the following product mixture:

| Product | Mole % |
|---|---|
| acetaldehyde | 78.5 |
| propylene oxide | 18.2 |
| allyl alcohol | 3.3 |

EXAMPLE NO. 2

The procedure of Example 1 was followed without $O_2$ purging; the $TiO_2$-deionized water suspension was placed under $N_2$ atmosphere in the presence of 0.1M $Cu(NO_3)_2 \cdot 2\frac{1}{2}\ H_2O$. The propylene flow rate through the reaction mixture was 12 cc/min. Gas chromatagraphic analysis of the aqueous suspension after filtration showed the following product mixture:

| Product | Mole % |
|---|---|
| acetaldehyde | 10.3 |
| propylene oxide | 41.4 |
| propionaldehyde | 10.3 |
| acrolein | 24.1 |
| allyl alcohol | 13.8 |

EXAMPLE NO. 3

The propylene oxidation procedure of Example 1 was followed with 0.1M $Cu(NO_3)_2 \cdot 2\frac{1}{2}\ H_2O$ having been added to the $TiO_2$-deionized water suspension to form the reaction mixture. Gas chromatographic analysis of the aqueous suspension after filtration showed the following product mixture:

| Product | Mole % |
|---|---|
| acetaldehyde | 31.6 |
| propylene oxide | 51.2 |
| propionaldehyde | 6.2 |
| acrolein | 9.9 |
| allyl alcohol | 1.1 |

EXAMPLE NO. 4

The propylene oxidation procedure of Example 1 was followed using 100 mg platinized-$TiO_2$ with oxygen as the oxidant. Gas chromatographic analysis of the aqueous suspension after filtration showed the following product mixture:

| Product | Mole % |
|---|---|
| acetaldehyde | 18.5 |
| propylene oxide | 2.9 |
| allyl alcohol | 0.34 |
| propionaldehyde | 0.74 |

EXAMPLE NO. 5

The propylene oxidation procedure of Example 1 was followed, without $O_2$ purging, under $N_2$ atmosphere and with the use of 100 mg platinized-$TiO_2$ semiconductor powder with the place of $TiO_2$ powder. Gas chromatographic analysis of the aqueous suspension after filtration showed the following product mixture:

| Product | Mole % |
|---|---|
| acetaldehyde | 1.0 |
| propylene oxide | 28.2 |
| propionaldehyde | 62.6 |
| allyl alcohol | 8.2 |

EXAMPLE NO. 6

The propylene oxidation procedure of Example 2 was followed using 100 mg platinized-$TiO_2$, under $N_2$ atmosphere in the presence of 0.1M $Cu(NO_3)_2 \cdot 2\frac{1}{2}\ H_2O$. Gas chromatographic analysis of the aqueous suspension after filtration showed the following product mixture:

| Product | Mole % |
|---|---|
| acetaldehyde | 0.7 |
| propylene oxide | 5.4 |
| allyl alcohol | 1.1 |
| propionaldehyde | 1.6 |
| acrolein | 1.9 |

EXAMPLE NO. 7

The propylene oxidation procedure of Example 1 was followed using $MoO_3$ modified $TiO_2$. Gas chromatographic analysis of the aqueous suspension after filtration showed the following product mixture:

| Product | Mole % |
|---|---|
| acetaldehyde | 10.4 |
| propylene oxide | 58.1 |
| acrolein | 31.5 |

The products resulting from Examples No. 1 through 7 have been summarized in Table I. The photocatalyst employed is designated under the column Components; yield for each oxidation product is reported numerically in terms of mol formed in a three hour period; selectivity in mole percent is the second number, enclosed in parentheses, and $Cu^{2+}$ where designated was 0.1M $Cu(NO_3)_2 \cdot 2\frac{1}{2}\ H_2O$.

TABLE I

Photooxidation of Propylene on $TiO_2$ Catalysts[a]

| Ex. No. | Components[b] | Acetaldehyde | Propylene oxide | Allyl Alcohol | Propionaldehyde | Acrolein |
|---|---|---|---|---|---|---|
| 1 | $TiO_2/O_2$ | 28.4(78) | 6.6(18) | 1,2(4) | — | — |
| 2 | $TiO_2/N_2/Cu^{2+}$ | 1.2(10) | 4.8(41) | 1.6(14) | 1.2(10) | 2.9(24) |
| 3 | $TiO_2/O_2/Cu^{2+}$ | 12.8(32) | 20.7(51) | 0.45(1.1) | 2.5(6.2) | 4.0(10) |
| 4 | $Pt—TiO_2/O_2$ | 18.5(82) | 2.9(13) | 0.34(1.5) | 0.74(3.3) | — |
| 5 | $Pt—TiO_2/N_2$ | 0.3(1) | 3.3(28) | 2.4(8.2) | 18.4(63) | — |
| 6 | $Pt—TiO_2/N_2/Cu^{2+}$ | 0.7(6.5) | 5.4(50) | 1.1(10) | 1.6(15) | 1.9(18) |
| 7 | $TiO_2/MoO_3/O_2$ | 10.4 | 58.1 | — | — | 31.5 |

[a] 500 W lamp, 3 hours exposure, 25° C.
[b] 100 mg $TiO_2$, 10 ml $H_2O$.

As can be seen with reference to Table I, large amounts of acetaldehyde were formed utilizing $TiO_2$ in $O_2$, without an A component, Example No. 1. Some oxidation occurred without $O_2$ by utilizing the $Cu^{2+}$ ion as an oxidant, Example No. 2, while for Example No. 3, greater amounts of oxidation products were obtained utilizing both $O_2$ and $Cu^{2+}$ ion as oxidants. Metallized $TiO_2$ was employed for Examples No. 4 and 5 with $O_2$ and $N_2$ respectively, with acetaldehyde favored under $O_2$ and propionaldehyde favored under $N_2$. For Example No. 6, No. 5 was repeated in the presence of $Cu^{2+}$ ion and for Example No. 7, a $MoO_3$ modified $TiO_2$ resulted in the production of the greatest amount of propylene oxide.

In the next three examples, Nos. 8 through 10, the effect of a mixed solvent media is reported, the solvent comprising water and acetonitrile in varying proportions. For Example No. 11, acetonitrile alone was employed. The catalyst component for the four examples was $TiO_2$ without any redox couple. Gas chromatographic analysis of the suspension of each example after filtration was again conducted and the product mixture has been reported in Table II. Product yield is given in mol formed in a three hour period.

EXAMPLE NO. 8

The propylene oxidation procedure of Example No. 1 was followed using 15 ml of a 50:50 water:acetonitrile solvent mixture.

EXAMPLE NO. 9

The propylene oxidation procedure of Example No. 1 was followed using 15 ml of a 12:28 water:acetonitrile solvent mixture.

EXAMPLE NO. 10

The propylene oxidation procedure of Example No. 1 was followed using 15 ml of a 20:80 water:acetonitrile solvent mixture.

EXAMPLE NO. 11

The propylene oxidation procedure of Example 1 was followed using 10 ml of acetonitrile as solvent in place of deionized water.

TABLE II

Propylene Oxidation in Mixed Water-Acetonitrile Media[a]

| Ex. No. | Component[b] | $H_2O$:MeCN[c] | Acetaldehyde | Propylene Oxide | Acrolein |
|---|---|---|---|---|---|
| 8 | $TiO_2/N_2$ | 50:50 | 17.7 | 18.7 | 30.6 |
| 9 | $TiO_2$ $N_2$ | 12:88 | 35.7 | 17.4 | 70.8 |
| 10 | $TiO_2/N_2$ | 20:80 | 47.9 | 19.6 | 76.0 |
| 11 | $TiO_2/N_2$ | 0:100 | | | |

[a]500 W lamp, 3 hours exposure, 25° C.
[b]100 mg $TiO_2$.
[c]solvent mixture.

As can be seen by comparing Example No. 1 with Examples No. 8 through 11, acrolein was produced when acetonitrile was present in the solvent media, and generally, the yield of acetaldehyde and propylene oxide was increased.

Finally, in Examples No. 12 and 13 the oxidation of a cyclic olefin was conducted as follows:

EXAMPLE NO. 12

Cyclohexene oxidation was carried out in aqueous solvent media. A stirred suspension of 10 ml water, 100 mg of $TiO_2$ semiconductor powder, and 0.2 ml cyclohexene was illuminated with a 500 watt mercury lamp for about 3 hours. This procedure resulted primarily in the formation of 2-cyclohexene-1-one (28 $\mu$mol) with a minor amount of cyclohexene oxide (0.3 $\mu$mol).

EXAMPLE NO. 13

When 0.1 mol $Cu^{2+}$ion was present during illumination, the formation of cyclohexene oxide was enhanced (8 $\mu$mol); (18 $\mu$mol) 2-cyclohexene-1-one was formed.

Based upon the foregoing results, it can be seen that the process of the present invention is able to effect selective oxidation of olefins at ambient temperatures i.e., about 25° C.; and that it is highly selective to desirable products such as epoxides, aldehydes, alcohols and ketones depending upon the selection of variables. Variables, in addition to the basic semiconductor photocatalyst $B_yC_z$ selected, include the optional use of the A component elements and their manner of employment, the use of optional metallizing elements, the solvent system selected, and the oxidants selected.

Thus, it is to be understood that all of the variables, those disclosed as well as those falling within the existing skill in the art, fall within the scope of the claimed invention and that the subject invention is in no way limited by the examples and respective tables set forth herein. These have been provided merely to provide a demonstration of operability and, therefore, the selection of olefins, solvents, oxidants, processing steps and parameters and the like can readily be determined without departing from the spirit of the invention herein disclosed and described. Moreover, the scope of the invention shall include all modifications and variations that fall within the scope of the attached claims.

We claim:

1. A process for the selective oxidation of olefins comprising the steps of:

forming a suspension of a semiconductor powder in a solvent media, said semiconductor powder having the general formula $A_xB_yC_z$ where A is selected from Bi, Sn, Pt, Pd, Cu, Fe, W, V, Sb, Mo, Ru or Ag and mixtures thereof; B is Te or W and mixtures thereof; C is O or S; x equals 0 to 5; y equals 1 to 3; and z is a number necessary to satisfy the other elements;

adding an olefin to said suspension in the presence of an oxidant to form a mixture; and photochemically activating said mixture with illumination having an energy at least equal to the band gap of said semiconductor powder wherein the selectivity is controlled by the selection of A, of said solvent and of said oxidant.

2. A process for the selective oxidation of olefins, as set forth in claim 1, said process being carried out at about ambient temperature and with gentle agitation of said mixture.

3. A process for the selective oxidation of olefins, as set forth in claim 1, wherein said solvent is water and said oxidant is $O_2$.

4. A process for the selective oxidation of olefins as set forth in claim 3, wherein said olefin is propylene.

5. A process for the selective oxidation of olefins, as set forth in claim 1, wherein said A component forms a solid matrix with said semiconductor powder.

6. A process for the selective oxidation of olefins, as set forth in claim 1, wherein said A component is introduced by addition of a salt thereof to said suspension.

7. A process for the selective oxidation of olefins as set forth in claim 6, wherein said solvent is water and said oxidant comprises $O_2$ and $Cu^{2+}$.

8. A process for the selective oxidation of olefins, as set forth in claim 7, wherein said olefin is propylene.

9. A process for the selective oxidation of olefins, as set forth in claim 8, wherein said olefin is propylene and the process is conducted in an inert atmosphere of $N_2$.

10. A process for the selective oxidation of olefins as set forth in claim 1, wherein x is 0 and said semiconductor powder is metallized.

11. A process for the selective oxidation of olefins as set forth in claim 1, wherein said A component is Cu and said semiconductor powder is metallized.

12. A process for the selective oxidation of olefins, as set forth in claim 1, wherein said solvent is water said oxidant is $O_2$ and said olefin is cyclohexene.

13. A process for the selective oxidation of olefins as set forth in claim 1, said illumination being derived from a 500 watt mercury lamp.

14. A process for the selective oxidation of olefins, as set forth in claim 1, wherein said oxidant is selected from the group consisting of $O_2$, $H^+$, $Cu^{2+}$, $Fe^{3+}$, $V^{5+}$, $Sn^{4+}$ and mixtures thereof.

15. A process for the selective oxidation of olefins, as set forth in claim 1, wherein said olefins are selected from the group consisting of substituted linear and cyclic compounds having from about two to 20 1 carbon atoms.

16. A process for the selective oxidation of olefins, as set forth in claim 1, wherein said solvents are selected from the group consisting of water, organic solvents for said olefins and mixtures thereof.

17. A process for the selective oxidation of olefins, as set forth in claim 1, wherein said semiconductor powder is metallized by an element selected from Pt, Pd, Cu or Ag.

18. A process for the selective oxidation of olefins comprising the steps of:

forming a suspension of a semiconductor powder in a solvent media, said semiconductor power having the general formula $A_xB_yC_z$ where A is selected from Bi or Cd and mixtures thereof; B is Te, Sb, Ti, Cd, Mo, V or W and mixtures thereof; C is O or S; x equals 0 to 5; y equals 1 to 3; and z is a number necessary to satisfy the other elements;

adding an olefin to said suspension in the presence of an oxidant to form a mixture; and photochemically activating said mixture with illumination having an energy at least equal to the band gap of said semiconductor powder wherein the selectivity is controlled by the selection of A, of said solvent and of said oxidant.

19. A process for the selective oxidation of olefins, as set forth in claim 18, said process being carried out at about ambient temperature and with gentle agitation of said mixture.

20. A process for the selective oxidation of olefins, as set forth in claim 18, wherein said solvent is water and said oxidant is $O_2$.

21. A process for the selective oxidation of olefins as set forth in claim 20, wherein said olefin is propylene.

22. A process for the selective oxidation of olefins, as set forth in claim 18, wherein said A component forms a solid matrix with said semiconductor powder.

23. A process for the selective oxidation of olefins, as set forth in claim 18, wherein said A component is introduced by addition of a salt thereof to said suspension.

24. A process for the selective oxidation of olefins as set forth in claim 18, wherein said solvent is water and said oxidant comprises $O_2$ and $Cu^{2+}$.

25. A process for the selective oxidation of olefins, as set forth in claim 18, wherein said olefin is propylene and the process is conducted in an inert atmosphere of $N_2$.

26. A process for the selective oxidation of olefins as set forth in claim 18, wherein x is 0 and said semiconductor powder is metallized.

27. A process for the selective oxidation of olefins, as set forth in claim 18, wherein said solvent is water, said oxidant is $O_2$ and said olefin is cyclohexene.

28. A process for the selective oxidation of olefins as set forth in claim 18, said illumination being derived from a 500 watt mercury lamp.

29. A process for the selective oxidation of olefins, as set forth in claim 18, wherein said oxidant is selected from the group consisting of $O_2$, $H^+$, $Cu^{2+}$, $Fe^{3+}$, $V^{5+}$, $Sn^{4+}$ and mixtures thereof.

30. A process for the selective oxidation of olefins, as set forth in claim 18, wherein said olefins are selected from the group consisting of substituted linear and cyclic compounds having from about two to 20 carbon atoms.

31. A process for the selective oxidation of olefins, as set forth in claim 18, wherein said solvents are selected from the group consisting of water, organic solvents for said olefins and mixtures thereof.

32. A process for the selective oxidation of olefins, as set forth in claim 18, wherein said semiconductor powder is metallized by an element selected from Pt, Pd, Cu or Ag.

* * * * *